United States Patent [19]
Masson

[11] Patent Number: 5,450,763
[45] Date of Patent: Sep. 19, 1995

[54] DEVICE FOR COLLECTING SAMPLES OF A LIQUID IN A TANK FOR IN A CHEMICAL REACTION VESSEL

[76] Inventor: Guy Masson, 1906 Chopin Dr., Baton Rouge, La. 70806

[21] Appl. No.: 196,127
[22] PCT Filed: Jun. 23, 1993
[86] PCT No.: PCT/CH93/00161
§ 371 Date: Feb. 17, 1994
§ 102(e) Date: Feb. 17, 1994
[87] PCT Pub. No.: WO94/01752
PCT Pub. Date: Jan. 20, 1994

[30] Foreign Application Priority Data
Jul. 2, 1992 [CH] Switzerland ................... 2078/92

[51] Int. Cl.⁶ ............................. G01N 1/10; G01N 1/12
[52] U.S. Cl. ............................. 73/864.31; 73/863.81; 73/864.73
[58] Field of Search ........... 73/863.81, 864.31, 864.32, 73/864.73, 863.83, 863.82, 863.84; 141/110, 111, 112; 222/356

[56] References Cited

U.S. PATENT DOCUMENTS

| | | |
|---|---|---|
| 1,494,631 | 5/1924 | Roberts ........................ 73/863.32 |
| 2,198,324 | 4/1940 | Wiggins . |
| 3,563,096 | 2/1971 | Kinkelaar ..................... 73/864.32 |
| 3,670,577 | 6/1972 | Singer ........................... 73/864.32 |
| 3,853,009 | 12/1974 | Sutherland ................... 73/864.32 |
| 4,196,627 | 4/1980 | Locher .......................... 73/864.31 |
| 5,029,484 | 7/1991 | Somers et al. ............... 73/863.81 |

FOREIGN PATENT DOCUMENTS

| | | |
|---|---|---|
| 718955 | 6/1931 | France . |
| 588790 | 11/1933 | Germany . |
| 5029484 | 5/1989 | U.S.S.R. . |

*Primary Examiner*—Hezron E. Williams
*Assistant Examiner*—Nashmiya Ashraf
*Attorney, Agent, or Firm*—Silverman, Cass & Singer

[57] ABSTRACT

An apparatus for collecting a sample of a liquid in a vessel. The apparatus includes a tube positioned vertically above the vessel, a cup for removing liquid from the vessel which has an inlet opening and an outlet opening, a device for displacing the cup vertically between a position in the vessel below the surface of the liquid, and another position in the tube above the vessel, a conduit branching off from the tube at a first point adjacent the raised position of the cup, a sample valve in the conduit for admitting liquid to a collector, and a mechanism for diverting liquid outflow from the cup into the conduit.

11 Claims, 4 Drawing Sheets

DEVICE FOR COLLECTING SAMPLES OF A LIQUID IN A TANK FOR IN A CHEMICAL REACTION VESSEL

BACKGROUND OF THE INVENTION

1. Field of the Invention

The present invention relates to a device for collecting samples of a liquid in a tank or in a chemical reaction vessel, and more particularly to a device comprising a cup, which cup is provided with a cavity and with openings for filling and for outflow, and which is fitted, so as to be moveable by the action of a piston, in a guide tube which is fitted onto a tank or onto a chemical reaction vessel.

2. Description of Related Art

Devices for the collection of samples are utilized in the chemical industry for collecting samples of those liquids which are contained in tanks or in chemical reaction vessels for the purpose of performing laboratory analyses. These liquids are most often very toxic and volatile; and consequently, the collecting of samples necessitates a great many precautions, on the one hand, to spare the user from having to come into contact with the toxic liquid, and, on the other hand, to prevent pollution resulting from the release of a toxic and volatile liquid into the surrounding air.

The heretofore known embodiments of devices for collecting samples present a great many disadvantages. In fact, the embodiments of prior art generally consist of devices provided with conduits which collect the liquid by means of suction mechanisms or aspirating pumps, all of which occasionally makes it impossible to collect the sample due to the fact that the liquid fails to rise in the collecting device when the reaction vessel is subjected to vacuum conditions or when the vapor tension of the liquid is low. There are embodiments utilizing gases which are intended to aspirate or to drive the sample of liquid to outside of the reaction vessel; however, these embodiments present a disadvantage linked to the use of a gas under pressure, the chief hazard of which may be the bursting of a seam or joint, which may constitute a grave peril for the operator in case the gas were to escape outwards. What is more: all these devices of prior art exhibit a major drawback in that they throw out into the atmosphere a significant quantity of polluted gases. An exemplified embodiment of a piston being displaceable in a tube is already known from U.S. Pat. No. 5,029,484; however, this device presents the disadvantage of not being able to function except in an open appliance—which is to say that it can only function correctly if the external pressure is equal to the pressure prevailing in the tank or in the chemical reaction vessel.

SUMMARY OF THE INVENTION

Thus, the object of the present invention consists in remedying the abovementioned disadvantages of the embodiments of prior art.

According to the principle of the invention, a cup provided with a cavity and with openings for filling and for outflow is fitted, so as to be moveable by the action of a piston, in a tube-which is fitted onto a tank or onto a chemical reaction vessel. When in its lowered position, the cup is immersed in the liquid which is contained in the tank, and the liquid makes its way into the cup through the openings for filling. Actuated by the piston, the cup is caused to rise in the tube until the outflow conduit is located above the level of a ring which acts as a collector. Both the dimensions and the angle of the outflow conduit are determined in such a way as to enable the liquid to flow from the cup by gravity as a continuous thin stream of liquid following the course of a parabola until it arrives onto the collector, which then conveys it into a sampling valve. The principle of the invention presents numerous advantages, foremost of which is the fact that it permits the sampling of liquids, regardless of whatever conditions of pressure and temperature may prevail in the interior of the reaction vessel. It makes possible the sampling of a liquid with a very low vapor tension or of a liquid subjected to vacuum conditions, and likewise even when the liquid is one that undergoes crystallization at room temperature. Another significant advantage consists in the fact that the particular construction design of the outflow conduit serves to facilitate the complete emptying of the cup, and yet another advantage consists in the fact that the layout of the sampling device permits the device as a whole to be emptied and drained entirely of the liquid, which liquid then returns directly into the tank or into the chemical reaction vessel. This advantage makes it possible to obtain a sample that is immediately representative of the liquid as it exists at the time of the next sampling. The principle of the invention presents the further advantage of making possible the collection of samples in the course of a distillation process or during a chemical reaction, without alteration of the pressure or vacuum prevailing in the interior of the reaction vessel. The slight loss of liquid which occurs during the passage from the lowered position of filling to the outflow position of the cup is negligible, because the changing of position is accomplished in a very brief period of time. The principle of the invention is also characterized particularly by the fact that the thin stream of liquid flows towards the collecting conduit by following the trajectory of a parabola.

BRIEF DESCRIPTION OF THE DRAWINGS

The attached drawings illustrate diagrammatically and by way of example the principles of the invention.

DESCRIPTION OF THE PREFERRED EMBODIMENTS

Figure 1:
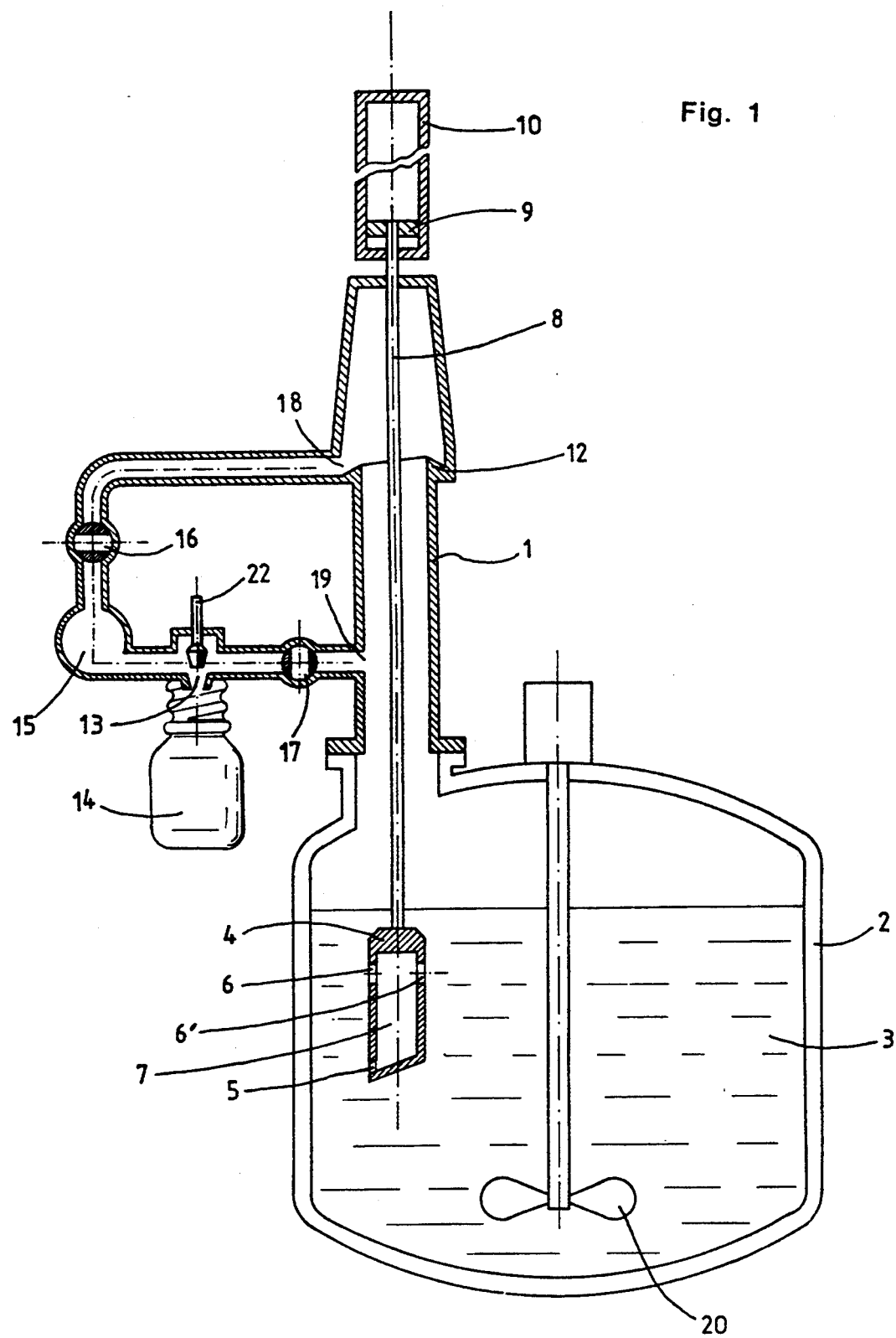
FIG. 1 is an overall lateral cutaway view of the entire sampling device in the position in which the cup undergoes filling.
Figure 2:
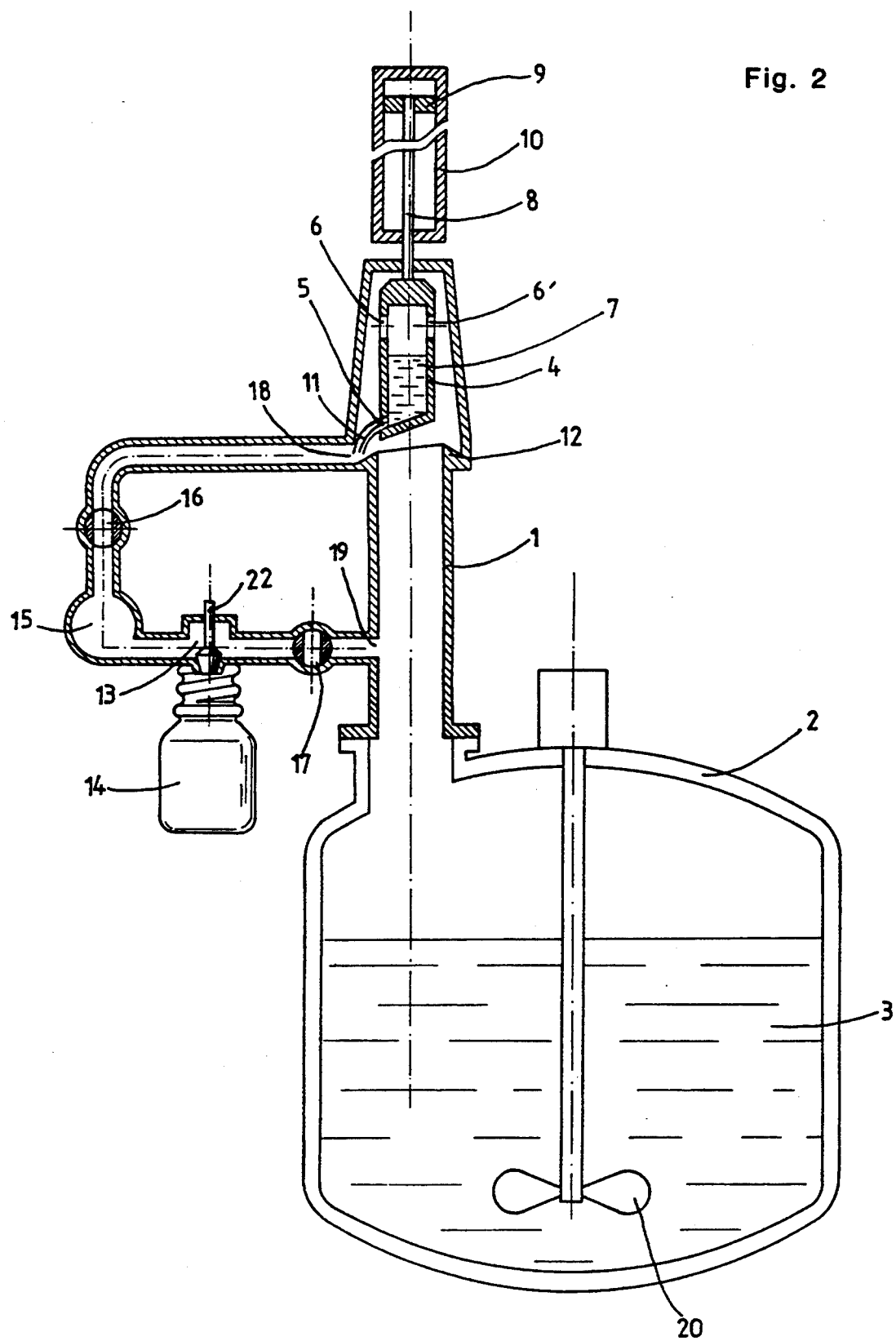
FIG. 2 is an overall lateral cutaway view of the sampling device in the position of outflow from the cup.

With reference to FIGS. 1 and 2, a guide tube 1 is fitted onto a chemical reaction vessel 2 which contains a liquid 3. A cup 4 is connected to a rod 8, which is itself connected to a moveable device, which latter is constituted, by way of example, by a piston 9 and a cylinder 10. Said cup 4 comprises a cavity 7, openings for filling 6 and 6' and an outflow conduit 5. Said tube 1 is provided with an intake opening 18 which constitutes an inlet conduit for the liquid and which is connected by an intake valve 16 to a sampling valve 13. Said tube 1 is also provided with an opening 19 which constitutes a conduit for emptying which is connected to a return valve 17, which latter is itself connected to the sampling-valve device 13. At the level of intake opening 18, the tube 1 is provided with a collector 12 which is constituted by a ring. A flow-inspection port 15 is emplaced between the intake valve 16 and the sampling valve 13. The liquid is collected in the receptacle 14 by pulling on the obturating needle 22. The liquid 3 contained in the tank 2 is kept in motion by a stirring device 20.

In its filling position, the cup is placed in the lowered position shown in FIG. 1, in which position the openings for filling 6 and 6' are located below the surface of the liquid 3, in such a way that the liquid fills the cavity 7 of the cup. As shown in FIG. 2, the intake valve 16 is actuated in the opened position and the piston 9 is actuated in such a way as to raise the cup into the raised position—that is to say, up to the position at which the outflow conduit 5 is located above the collector 12. In this position, the liquid flows from the cup 4 through the outflow conduit 5 and forms a thin stream which follows the trajectory of a parabola and which flows into the collector 12. The liquid then flows through valve 16 towards the sampling valve 13. The completion of the flow can be monitored in the flow-inspection port 15. Valve 16 is then closed; and, with the obturating needle 22 being pulled, the necessary liquid can flow into the receptacle 14. As soon as the quantity of liquid for sampling is deemed sufficient, the obturating needle 22 is returned to its closed position and valve 17 is opened in such a way as to empty the sampling device of the superfluous liquid, which liquid can now flow through opening 19 and through the tube 1 and return to the chemical reaction vessel. During passage from the lowered position of the cup to its raised position, a meager quantity of liquid may flow through the outflow conduit 5 and return into the chemical reaction vessel, all of which does not present any disadvantage since the speed at which the cup is displaced can be regulated in such a way that the greater portion of the liquid filling the cavity still remains in the cavity when the cup reaches its raised position.

Figure 3:
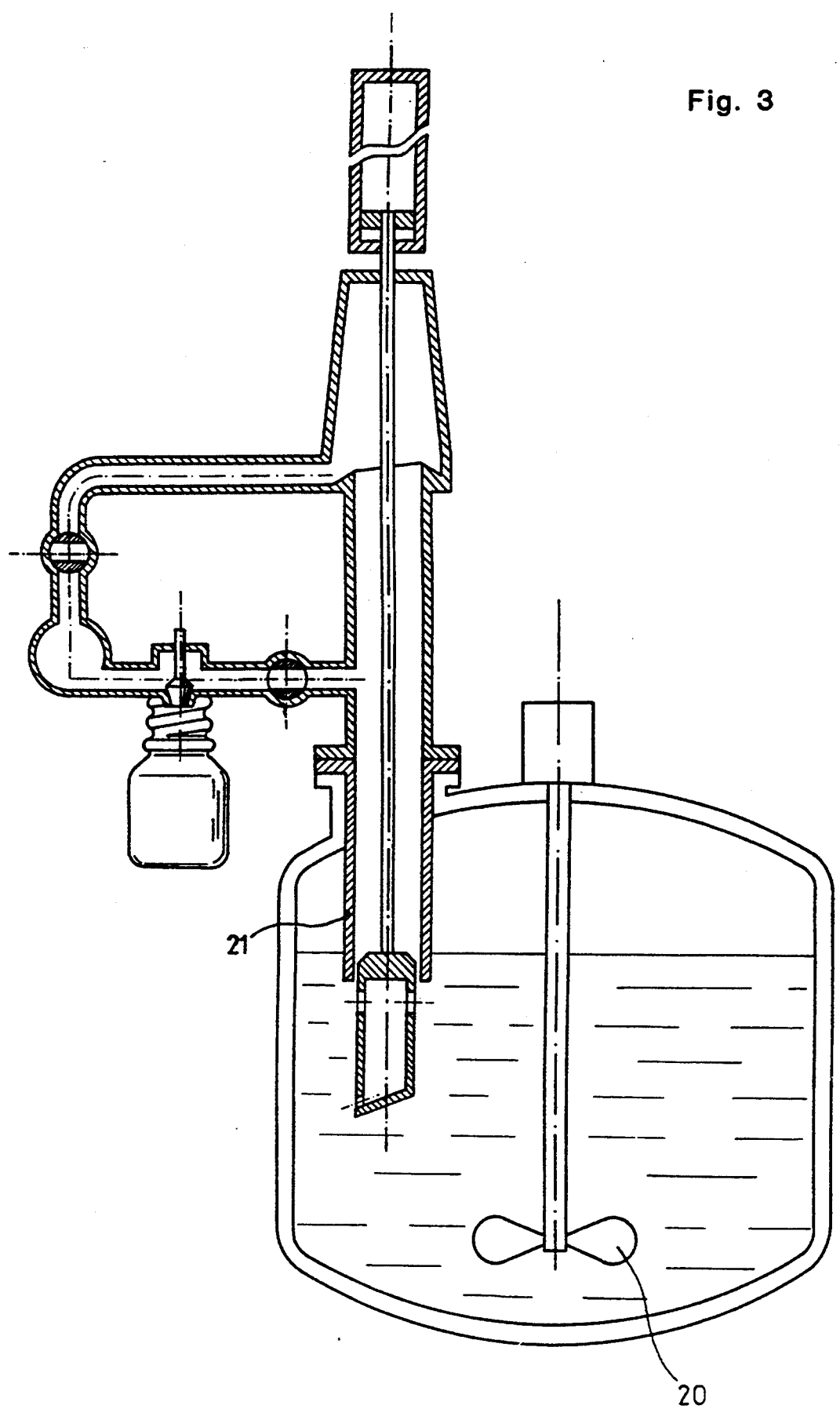
FIG. 3 is an overall lateral cutaway view of the device, showing an embodiment of the lower portion of a tube which is provided with a protective sheath.

FIG. 3 shows an embodiment which comprises a sheath 21 which is intended to protect the cup from those turbulences of the liquid that may be caused by the stirring device 20.

Figure 4:
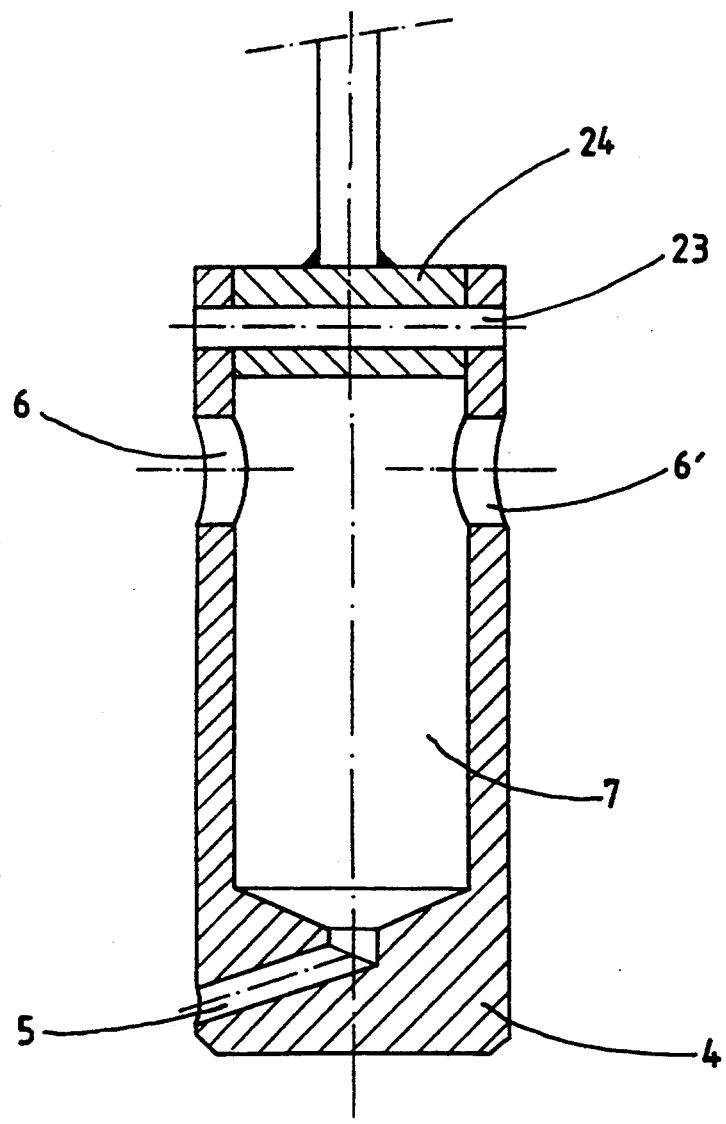
FIG. 4 is a detailed cutaway view of an embodiment of a cup.

FIG. 4 is a detailed view of the cup 4 which is provided with the cavity 7, the openings for filling 6 and 6' and the outflow conduit 5. The upper part of the cup is connected by a shaft 23 to a lower member 24 of the displacing mechanism.

FIGS. 1 and 2 show, by way of example, a displacing mechanism in the form of a piston which can be actuated by pneumatic means. The principle of the displacing mechanism is independent from the principle of the invention itself, inasmuch as the rod 8 which is connected to the cup may likewise be activated by a mechanical displacing device—with a toothed rack, for example—or by a magnetically operated device.

The sampling device as a whole can be constructed with various materials that are currently utilized in the chemical industry, for example, with stainless steel, the inert metals, enameled steel, teflon, glass, or with linings of fluorocarbon resin.

What is claimed is:

1. Apparatus for collecting a sample of a liquid contained in a vessel, comprising:
    a tube positioned vertically above the vessel;
    a cup for removing liquid from the vessel and comprising an inlet opening and an outlet opening;
    means for displacing the cup vertically between a first position in the vessel below the surface of the liquid, and a second position in the tube above the vessel;
    a conduit branching off from and in flow communication with said tube at a first point adjacent said second position;
    a sample valve in said conduit for selectively admitting liquid flowing through said conduit to a collecting means; and
    a means for diverting liquid outflow from said cup in said second position into said conduit.

2. Apparatus according to claim 1, additionally comprising an intake valve disposed in the conduit between the tube and the sample valve.

3. Apparatus according to claim 1, wherein the outlet opening is arranged at an angle in a lower portion of the cup to enable liquid flow out of the cup in a continuous thin stream.

4. Apparatus according to claim 1, wherein the diverting means has a conical shape and comprises a trough for recovery of liquid.

5. Apparatus according to claim 1, wherein said conduit is in flow communication with said tube at a second point below said first point to form a continuous path for flow of liquid and return of liquid to the vessel.

6. Apparatus according to claim 5, additionally comprising a return valve disposed between said sample valve and said second point.

7. Apparatus according to claim 1, wherein said means for displacing comprises a piston and cylinder, and a rod passing through the tube and connecting the piston to the cup.

8. Apparatus according to claim 1, wherein the tube is extended in a lower portion by a protective sheath.

9. Apparatus according to claim 1, wherein the vessel is a reaction vessel.

10. Apparatus according to claim 1, wherein the vessel is a tank.

11. Method for collecting a sample of liquid from a vessel, comprising the steps of:
    a) extending a tube vertically above the vessel;
    b) disposing a cup having an inlet opening and outlet opening in the vessel below the surface of the liquid, and permitting liquid to flow into the cup;
    c) disposing a conduit in flow communication with the tube at a first point and a second point below the first point;
    d) disposing in the conduit, sequentially between the first point and the second point, an internal intake valve, a sample valve for removing liquid from the conduit through an outlet, and an internal return valve;
    e) attaching a collection bottle to the outlet of the sample valve;
    f) raising the cup containing the liquid vertically to the first point in the tube, and permitting liquid to drain from the cup into the conduit, with the return valve and the sample valve closed, and the intake valve open;
    g) closing the intake valve and opening the sample valve, permitting a predetermined amount of liquid to flow into the collection bottle; and
    h) subsequently closing the sample valve and opening the return valve to permit any liquid remaining to return to the vessel.

* * * * *

UNITED STATES PATENT AND TRADEMARK OFFICE
CERTIFICATE OF CORRECTION

PATENT NO. : 5,450,763
DATED : September 19, 1995
INVENTOR(S) : Guy Masson

It is certified that error appears in the above-indentified patent and that said Letters Patent is hereby corrected as shown below:

Cover page and Column 1, line 3, in the title,
    change "FOR" to --OR--.

Signed and Sealed this

Fifth Day of December, 1995

Attest:

BRUCE LEHMAN

Attesting Officer

Commissioner of Patents and Trademarks